United States Patent
Shih

(10) Patent No.: US 9,253,994 B2
(45) Date of Patent: *Feb. 9, 2016

(54) METHODS AND COMPOSITIONS FOR IMPROVING GROWTH OF MEAT-TYPE POULTRY

(71) Applicant: North Carolina State University, Raleigh, NC (US)

(72) Inventor: Jason C. H. Shih, Cary, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/516,702

(22) Filed: Oct. 17, 2014

(65) Prior Publication Data

US 2015/0037458 A1    Feb. 5, 2015

Related U.S. Application Data

(63) Continuation of application No. 14/061,074, filed on Oct. 23, 2013, now Pat. No. 8,889,396, which is a continuation of application No. 13/035,652, filed on Feb. 25, 2011, now Pat. No. 8,642,313, which is a continuation of application No. 10/638,118, filed on Aug. 8, 2003, now Pat. No. 7,915,024.

(60) Provisional application No. 60/402,228, filed on Aug. 9, 2002.

(51) Int. Cl.
| | |
|---|---|
| A23K 1/165 | (2006.01) |
| A23K 1/00 | (2006.01) |
| A23K 1/18 | (2006.01) |
| A61K 38/48 | (2006.01) |

(52) U.S. Cl.
CPC ............ *A23K 1/009* (2013.01); *A23K 1/1653* (2013.01); *A23K 1/1826* (2013.01); *A61K 38/48* (2013.01)

(58) Field of Classification Search
None
See application file for complete search history.

(56) References Cited

U.S. PATENT DOCUMENTS

| | | | |
|---|---|---|---|
| 5,186,961 A | 2/1993 | Shih et al. | 426/2 |
| 5,612,055 A | 3/1997 | Bedford et al. | |
| 5,624,829 A | 4/1997 | Sanders et al. | 435/454 |
| 5,712,147 A | 1/1998 | Shih et al. | |
| 5,985,336 A | 11/1999 | Ivey et al. | |
| 6,221,406 B1 | 4/2001 | Meschonat et al. | |
| 6,329,001 B1 | 12/2001 | Ivey et al. | |
| 6,855,548 B2 | 2/2005 | Sjoeholm et al. | |
| 6,960,462 B2 | 11/2005 | Sjoeholm et al. | |
| 2004/0161448 A1 | 8/2004 | Sjoeholm et al. | |

FOREIGN PATENT DOCUMENTS

| | | | |
|---|---|---|---|
| EP | 0496361 A2 | 7/1992 | |
| EP | 1 257 176 B1 | 11/2002 | |
| JP | 06-505636 A | 6/1994 | |
| WO | WO 92/16113 | 10/1992 | |
| WO | WO 95/28850 A1 | 11/1995 | |
| WO | WO97/39130 | 10/1997 | ............ C12N 15/57 |
| WO | WO 01/58276 A2 | 8/2001 | |
| WO | WO03/010287 | 2/2003 | |

OTHER PUBLICATIONS

Mashed—definition of mashed by the Free Online Dictionary, Source URL: http://www.thefreedictionary.com/mashed, 1 pg, accessed Dec. 30, 2013.
Meal—definition of meal by the Free Online Dictionary, Source URL: http://www.thefreedictionary.com/meal, 4 pgs.
"An Analysis of the Automated Base-Calling Accuracy of the 373 DNA Sequencer", *Applied Biosystems, Inc.* 4 pages (1992).
Evans et al. "Subtilisins of *Bacillus* spp. hydrolyze keratin and allow growth on feathers", *Can. J. Microbiol.* 46(11):1004-1011 (2000).
Experimental Results comparing the amino acid sequences of PWD-1 and Alcalase and the molecular weights as determined by mass spectroscopy 4 pages, submitted Jul. 2, 2014.
Haensler at al. "Enzymatic Formation of Glu-Xaa and Asp-Xaa Bonds Using Glu/Asp-specific Endopeptidase from *Bacillus licheniformis* in Frozen Aqueous Systems", *J. Peptide Sci.* 6:366-371 (2000).
Jacobs et al. "Cloning, sequence and expression of subtilisin Carlsberg from *Bacillus licheniformis*", *Nucleic Acids Research* 13(24):8913-8926 (1985).
Jost et al. "Enzymes in Animal Nutrition", *Proceedings of the 1st Symposium* Kartause Ittingen, Switzerland pp. 149-151 (1993).
Lin et al. "Nucleotide Sequence and Expression of kerA, the Gene Encoding a Keratinolytic Protease of *Bacillus licheniformis* PWD-1", *Appl. Environ. Microbiol.* 61(4):1469-1474 (1995).
Onifade et al. "A Review: Potentials for Biotechnological Applications of Keratin-Degrading Microorganisms and Their Enzymes for Nutritional Improvement of Feathers and Other Keratins as Livestock Feed Resources", *Bioresource Technology* 66:1-11 (1998).
Siezen et al. "Subtilases: The superfamily of subtilisin-like serine proteases", *Protein Science* 6:501-523 (1997).
Table of Contents from Apr. 2003 edition of *Poultry Science* 82(4) listing Odetellah et al. (D17) as one of the papers published in that edition, 2 pgs.
Tindall et al. "Fidelity of DNA Synthesis by the *Thermus aquaticus* DNA Polymerase", *Biochemistry* 27:6008-6013 (1988).
Wang et al. "Fermentation production of keratinase from *Bacillus licheniformis* PWD-1 and a recombinant *B. subtilis* FDB-29", *J. Indust. Microb. Biotechnol.* 22:608-616 (1998).

(Continued)

*Primary Examiner* — Thane Underdahl
(74) *Attorney, Agent, or Firm* — Myers Bigel Sibley & Sajovec, P.A.

(57) ABSTRACT

The present invention provides methods of improving growth performance, improving the efficiency of feed utilization, increasing feed digestibility, and decreasing mortality of immature and developing animals receiving animal feed. Methods of producing a crude keratinase enzyme extract and animal feed supplements for achieving the same are also provided.

21 Claims, No Drawings

(56) References Cited

OTHER PUBLICATIONS

Ye et al. "Cloning, expression, purification, and characterization of a glutamate-specific endopeptidase from *Bacillus licheniformis*" *Protein Expression and Purification* 82:138-143 (2012).
Notice of Opposition corresponding to European Patent No. 1539226 dated Nov. 22, 2010, 34 pgs.
Notice of Opposition corresponding to European Patent No. 1539226 dated Dec. 20, 2010, 1 pg.
Proprietors Observations corresponding to European Patent No. 1539226 dated Jun. 29, 2011, 15 pgs.
Summons to attend Oral Proceedings corresponding to European Patent No. 1539226 dated May 29, 2012, 2 pgs.
Written Submissions corresponding to European Patent No. 1539226 dated Sep. 17, 2012, 103 pgs.
Main Request corresponding to European Patent No. 1539226 dated Oct. 5, 2012, 2 pgs.
Supplemental Submission corresponding to European Patent No. 1539226 dated Oct. 5, 2012, 46 pgs.
Proprietors' Statement of Grounds of Appeal corresponding to European Patent No. 1539226 dated Apr. 9, 2013, 70 pgs.
Reply to Appeal corresponding to European Patent No. 1539226 dated Aug. 15, 2013.
Minutes of the Oral Proceedings corresponding to European Patent No. 1539226 dated Nov. 29, 2012, 51 pgs.
Decision to Revoke corresponding to European Patent No. 1539226 dated Nov. 29, 2012, 2 pgs.
Issues to be discussed at Oral Proceedings corresponding to European Patent No. 1539226 dated Dec. 11, 2013, 9 pgs.
Chicken Feed: Feed Recipes from Chicken Feed: The world of Chickens. Available Feb. 5, 2001 http://web.archive.org/web/20010205053600/http://www.lionsgrip.com/recipes.html, 8 pgs.
Suh et al. "Characterization of a Keratinolytic Serine Protease from Bacillus subtilis KS-1", *J. Protein Chemistry* 20(2):165-169 (2001).
Bressollier et al. "Purification and Characterization of a Keratinolytic Serine Proteinase from *Streptomyces albidoflavus*", *Applied and Environmental Microbiology* p. 2570-2576 (1999).
Boeckle et al. "Characterization of a Keratinolytic Serine Proteinase from *Streptomyces pactum* DSM 40530", *Applied and Environmental Microbiology* p. 3705-3710 (1995).
Yu et al. "Amino Acid Composition and Specificity sf a Keratinase of Trichophyjon mentagrophytes", *Archives of Biochemistry and Biophysics* 135:363-370 (1969).
"Mash," The American Heritage® Dictionary of the English Language, Fourth Edition. Houghton Mifflin Company, 2004, 1 pg Answers.com Jul. 20, 2010.http://www.answers.com/topic/mash.
Pettersson et al.,"Enzyme supplementation of a poultry diet containing rye and wheat", *British Journal of Nutrition*, (1989), vol. 62, pp. 139-149.
Zanella et al., "Effect of enzyme supplementation of broiler diets based on corn and soybeans", *Poultry Science*, (1999) vol. 78, pp. 561-568.
"Change from Broiler Starter to Grower Diets at 14 Days Possible. Poultry Fact Sheet.," Nova Scotia Department of Agriculture and Fisheries, www.gov.ns.oa/nsaf, 1-4 (2001).
"Methods in Enzymology: Gene Expression Technology," Edited by David V. Goeddel, Academic Press, Inc., Harcourt Brace Jovanovich, Publishers, 185, Title Page.
Albertini et al., "Amplification of a Chromosomal Region in *Bacillus subtilis*," *Journal of Bacteriology*, 162:3 1203-1211 (Jun. 1985).
Bolhuis et al., "*Bacillus subtilis* can Modulate its Capacity and Specificity for Protein Secretion Through Temporarily Controlled Expression of the sips Gene for Signal Peptidase I," *Molecular Microbiology*, 22:4 605-618 (1996).
Bolhuis et al., "Evaluation of Bottlenecks in the Late Stages of Protein Secretion in *Bacillus Subtilis*," *Applied and Environmental Microbiology*, 65:7 2934-2941 (Jul. 1999).
Bradford, Marion M., "A Rapid and Sensitive Method for the Quantitation of Microgram Quantities of Protein Utilizing the Principle of Protein-Dye Binding," *Analytical Biochemistry*, 72: 248-254 (1976).
Bron et al., "Segregational Instability of pUB110-Derived Recombinant Plasmids in *Bacillus subtillis*," *Plasmid*, 14: 235-244 (1985).
Carter, Scott David, "Bacterial Keratinase: Assay Development and Nutritional Application," Dissertation submitted to the Graduate Faculty of North Carolina State University (1998). Abstract.
Chang et al., "Phenotypic Expression in *E. coli* of a DNA Sequence Coding for Mouse Dihydrofolate Reductase," *Nature*, 275: 617-624 (Oct. 19, 1978).
Daniels, G., "The Digestion of Human Hair Keratin by *Microsporum cani* Bodin," *J. gen, Microbiol.*, 8: 289-294 (1953).
de Boer et al., "On the Industrial Use of *Bacillus licheniformis*: A Review," *Applied Microbiology and Biotechnology*, 40:5 595-598 (Jan. 1994).
de Boer et al., "The *tac* Promoter: A Functional Hybrid Derived from the *trp* and *lac* Promoters," *Proc. Natl. Acad. Sci.*, 80: 21-25 (Jan. 1983).
Diderichsen et al., "Cloning and Expression of an Amylase Gene from *Bacillus stearothermophilus*," *Res. Microbiol.*, 142:7-8 793-796 (Sep.-Oct. 1991), Abstract.
Driessen, A.J.M., "How Proteins Cross the Bacterial Cytoplasmic Membrane," *J. Membrane Biol.*, 142: 145-159 (1994).
Goeddel et al., "Direct Expression in *Escherichia coli* of a DNA Sequence Coding for Human Growth Hormone," *Nature*, 281: 544-548 (Oct. 18, 1979).
Goeddel et al., "Synthesis of Human Fibroblast Interferon by *E. coli*," *Nucleic Acids Research*, 8:18 4057-4074 (1980).
Goktan, D., "Rate of Decomposition of Keratinous Material Used by Various Organisms," *Mikrobyiyo, Bul.*, 18:3 137-144 (Jul. 1984). Abstract.
Holland et al., "Isolation and Identification of Yeast Messenger Ribonucleic Acids Coding for Enolase, Glyceraldehyde-3-Phosphate Dehydrogenase and Phosphoglycerate Kinase," *Biochemistry*, 17:23 4900-4907 (1978).
Jensen et al., "Improvement in the Nutritional Value of Barley for Chicks by Enzyme Supplementation," *Research Notes*, 919-921 (Apr. 11, 1957).
Kawamura et al., "Construction of a *Bacillus subtilis* Double Mutant Deficient in Extracellular Alkaline and Neutral Proteases," *Journal of Bacteriology*, 160:1 442-444 (Oct. 1984).
Kingsman et al., "Replication in *Saccharomyces cervisiae* of Plasmid pBR313 Carrying DNA from the Yeast *trpl* Region," Department of Biological Sciences, University of California, Santa Barbara (1979).
Kontinen et al., "The PrsA Lipoprotein is Essential for Protein Secretion in *Bacillus subtilis* and Sets a Limit for High-Level Secretion," *Molecular Microbiology*, 8:4 727-737 (1993).
Laemmli, U.K., "Cleavage of Structural Proteins During the Assembly of the Head of Bacteriophage T4," *Nature*, 227: 680-685 (Aug. 15, 1970).
Lin et al., "Purification and Characterization of a Keratinase from a Feather-Degrading *Bacillus licheniformis* Strain," *Applied and Environmental Microbiology*, 58:10 3271-3275 (Oct. 1992).
Molyneux, G.S., "The Digestion of Wool by a Keratinolytic Bacillus," *Bacterial Digestion of Wool*, 274-281 (1959).
Noval et al., "Decomposition of Native Keratin by *Streptomyces fradiae*," Institute of Microbiology, Rutgers, The State University, New Brunswick, New Jersey, 77: 251-263 (1959).
Odetallah et al., "Effect of Keratinase on Growth Performance of Broiler Chicks Fed Starter Diets," *Abstracts: International Poultry Scientific Forum*, 45 (Jan. 14-15, 2002).
Odetallah et al., "Keratinase in Starter Diets Improves Growth of Broiler Chicks," *Poultry Science*, 82: 664-670 (2003).
Odetallah, Nasser Hussein, "Dietary Enzyme Supplementation to Alleviate Enteric Disorders in Turkeys," Dissertation submitted to the Graduate Faculty of North Carolina State University (2000). Title Page.
Primrose et al., "Isolation of Plasmid Deletion Mutants and Study of Their Instability," *Plasmid*, 6: 193-201 (1981).
Rotter et al., "Evaluation of Three Enzymic Methods as Predictors of in-vivo Response to Enzyme Supplementation of Barley-Based Diets when Fed to Young Chicks," *J Sci Food Agric*, 19-27 (1989).
Sambrook et al., "Molecular Cloning: A Laboratory Manual," Third Edition, Cold Spring Harbor Laboratory Press, New York (2001). Title Page.

(56) References Cited

OTHER PUBLICATIONS

Sarath et al., "Chapter 3: Protease Assay Methods," 25-55.
Smith Jr., Tom W., "Feed Chickens Properly," Cooperative Extension Service, Mississippi State University, 1-2.
Stinchcomb et al., "Isolation and Characterisation of a Yeast Chromosomal Replicator," *Nature*, 282: 39-43 (Nov. 1, 1979).
Towbin et al., "Electrophoretic Transfer of Proteins from Polyacrylamide Gels to Nitrocellulose Sheets: Procedure and Some Applications," *Proc. Natl. Acad. Sci.*, 76:9 4350-4354 (Sep. 1979).
Tschumper et al., "Sequence of a Yeast DNA Fragment Containing a Chromosomal Replicator and the *TRPI* Gene," *Gene*, 10: 157-166 (1980).
van der Laan et al., "Cloning, Characterization, and Multiple Chromosomal Integration of a *Bacillus* Alkaline Protease Gene," *Applied and Environmental Microbiology*, 57:4 901-909 (Apr. 1991).
Brenes et al. "Effect of Enzyme Supplementation on the Nutritional Value of Raw, Autoclaved, and Dehulled Lupins (*Lupinus albus*) in Chicken Diels", *Poultry Science* 72:2281-2293 (1993).
Statutory declaration affirming the publication date of the first reference, Product Sheet Bio-Feed Pro.

METHODS AND COMPOSITIONS FOR IMPROVING GROWTH OF MEAT-TYPE POULTRY

CROSS REFERENCE TO RELATED APPLICATIONS

This application is a continuation application of U.S. patent application Ser. No. 14/061,074, filed Oct. 23, 2013, issued as U.S. Pat. No. 8,889,396 on Nov. 18, 2014, which is a continuation application of U.S. patent application Ser. No. 13/035,652, filed Feb. 25, 2011, issued as U.S. Pat. No. 8,642,313 on Feb. 4, 2014, which is a continuation application of U.S. patent application Ser. No. 10/638,118, filed Aug. 8, 2003, issued as U.S. Pat. No. 7,915,024 on Mar. 29, 2011, which claims the benefit of U.S. Provisional Application Ser. No. 60/402,228 filed Aug. 9, 2002, the disclosures of which are incorporated herein by reference in their entirety.

STATEMENT OF FEDERAL SUPPORT

Research directed to this invention is supported in part by US Department of Agriculture Small Business Innovation Research Grant No. 2002-33610-11850. The Government has certain rights in this invention.

FIELD OF THE INVENTION

The present invention relates to methods of improving growth performance of immature and developing animals receiving animal feed and animal feed supplements for achieving the same.

BACKGROUND OF THE INVENTION

Broiler chick starter diets contain a considerable amount of crude protein. Most of the crude protein is obtained from traditional feed ingredients such as soybean meal. Approximately 90% of the crude protein present in soybean meal (48% crude protein content) is highly digestible for poultry (National Research Council (1994). Nutrient requirements of poultry. 9$^{th}$ revised Ed. National Academy Press, Washington, D.C.). Although the traditional corn-soybean meal broiler starter diets are considered highly digestible, they often contain a variety of complex proteins that are not easily digested by a young chick due to the lack of necessary innate enzymes at early stages of life (Uni, et al, (1999) Poultry Sci. 78: 215-222). Inclusion of proteases in broiler diets has been suggested, but much of the early work with protease addition to cereal grain-based diets did not result in any improvements in bird performance (Jensen, et al. (1957) Poultry Sci. 36: 919-921).

More recently, enzyme supplementation of poultry diets with enzyme mixtures, including proteases and amylases, has produced some improvements in growth performance (Greenwood, et al, (2002) Poultry Sci. 81 (Suppl. 1): 25; Burrows, et al. (2002) Poultry Sci, 81 (Suppl. 1): 29; Short, et al. (2002) Poultry Sci. 81 (Suppl. 1): 136). Supplementing a corn-soybean broiler starter diet with an enzyme preparation containing a mixture of xylanase, protease, and amylase resulted in improvements in body weight at 14 and 42 days of age with no significant effects on feed conversion ratio (Greenwood, at al. (2002) supra). Upon supplementing corn-soy based duck diets with the same enzyme mixture, the enzyme supplementation resulted in improvements in body weight gain and feed conversion ratio (Burrows, et al. (2002) supra).

Poultry feed further contains some complex antinutritional and/or indigestible compounds. Some of these compounds, such as the nonstarch polysaccharides, absorb water into a viscous mass within the chyme from which nutrients are not readily absorbed (Odetallah, 2000; Odetallah, et al. (2002) supra). As thyme viscosity increases, the rate of diffusion of digestive enzymes and nutrients decreases, thus impeding nutrient absorption by the enterocyte. Fat micelle formation and absorption also decrease as chyme viscosity increases, thus impairing absorption of many of the fat-soluble compounds, including fat-soluble vitamins, pigments, and lipids (Ferket and Veldkamp (1999) In: Proceedings of the 1998 World Poultry Science Association, pgs 43-52). Therefore, viscosity reduction achieved by endolytic enzyme activity may play a role in the improvement seen in young chicks fed high-viscosity cereals, and the relative effectiveness of various enzymes appears to be related to their viscosity-reducing capability (Rotter, et al. (1990) J. Sci. Food Agric. 50:19-27).

PWD-1 keratinase is an enzyme that was originally purified from the growth medium of Bacillus licheniformis PWD-1 (Williams, et al. (1990) Appl. Environ. Microbial. 56:1509-1515; Lin, et al. (1992) Appl. Environ Microbial. 58:3271-3275). PWD-1 keratinase hydrolyzes a broad range of protein substrates including casein, collagen, elastin and keratin (Shih (2001) In: Proceedings International Conference of Agricultural Science and Technology, Beijing, China, pgs 244-247). PWD-1 keratinase has been used to produce hydrolyzed feather meal by incubating commercial feather meal with cell-free keratinase overnight (Carter (1998) Bacterial Keratinase: Assay development and nutritional application. Ph.D. Thesis, North Carolina State University, Raleigh, N.C.). See also U.S. Pat. Nos. 4,908,220; 5,186,961; and 5,063,161 to Shih et al.

In spite of the foregoing, there remains a need for additional methods of enhancing growth performance of broiler chicks and animal feed supplements that accomplish the same,

SUMMARY OF THE INVENTION

The present invention provides methods and compositions that enhance growth performance of immature and developing animals receiving animal feed.

An aspect of the invention relates to a method of growing meat-type poultry comprising feeding meat-type poultry a corn-soybean meal feed as a poultry diet wherein the feed further comprises keratinase in an amount effective to enhance the weight gain of meat-type poultry.

Another aspect of the invention relates to a method of growing meat-type poultry comprising feeding meat-type poultry a corn-soybean meal feed as a starter diet wherein the feed further comprises keratinase in an amount effective to enhance the weight gain of the meat-type poultry.

A further aspect of the invention relates to a method of improving the efficiency of feed utilization of an animal feed in meat-type poultry comprising feeding meat-type poultry a corn-soybean meal feed as a poultry diet wherein the feed further comprises keratinase in an amount effective to improve the efficiency of feed utilization of an animal feed in meat-type poultry.

An additional aspect of the present invention relates to a method of increasing the digestibility of an animal feed in meat-type poultry comprising feeding meat-type poultry a corn-soybean meal feed as a poultry diet wherein the feed further comprises keratinase an amount effective to increase the digestibility of an animal feed in meat-type poultry.

Another aspect of the invention relates to a method of reducing mortality in meat-type poultry comprising feeding meat-type poultry a corn-soybean meal feed as a starter diet wherein the feed further comprises keratinase in an amount effective to reduce mortality of meat-type poultry.

A further aspect of the invention relates to an animal feed consisting essentially of keratinase, protein, and carbohydrate.

An additional aspect of the invention relates to a method of producing crude keratinase enzyme extract.

The present invention further relates to improving the nutritional status of a hatchling, and thereby increasing disease resistance and survivability of the immature bird to achieve a greater level of growth performance meat-type poultry.

DETAILED DESCRIPTION OF THE INVENTION

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all technical and scientific terms used herein have the same meaning as commonly understood by one of ordinary skill in the art to which this invention belongs.

All publications, U.S. patent applications, U.S. patents and other references cited herein are incorporated by reference in their entireties.

As used herein, the term "meat-type poultry" refers to any avian species that is produced or used for meat consumption as understood by one skilled in the art. Examples of such avian species include, but are not limited to, chickens, turkeys, ducks, geese, quail, pheasant, ratites, and the like.

As used herein, the term "immature bird" refers to a member of the avian species that lacks complete growth, differentiation, or development. Such members can have the potential capacity to attain a definite mature form or state. An immature bird can be from about 1 to about 50 days old, preferably about 1 to about 21 days old, and more preferably about 1 to about 5 days old, or can have a body weight comparable to birds within these ranges.

As used herein, the term "developing bird" refers to a member of the avian species that is older or weighs more than an immature bird.

As used herein, the term "mature bird" refers to a member of the avian species that is older or weighs more than a developing bird.

As used herein, the term "broiler chick" refers to any immature chicken produced or eventually used for meat consumption.

As used herein, the term "poultry diet" refers to a diet that can be administered to a member of the avian species to promote and maintain growth of the bird. A poultry diet can contain sources of protein, vitamins, minerals, energy such as fat, carbohydrates, and additional protein, antibiotics, and other substances or compounds known to be included in animal feeds, in particular, poultry feeds. Poultry diet is inclusive of, but not limited to, a starter diet, a grower-type diet, and a finisher-type diet. A "starter diet" refers to a diet that can be administered to an animal starting from birth or hatch until a desired age and/or weight is obtained. A "grower-type diet" refers to a diet that can be administered to an animal upon completion of the starter growth phase. A "finisher-type diet" refers to a diet that can be administered to an animal during the period of development through the time of slaughter.

As used herein, the terms "growth" or "growth performance" refer to increases in either, or both, weight and size (e.g., height, width, diameter, circumference, etc.) over that which would otherwise occur without implementation of the methods and/or administration of the compositions of the present invention. Growth can refer to an increase in the mass (e.g., weight or size) of the entire animal or of a particular tissue (e.g., muscle tissue in general or a specific muscle). Alternatively, growth can indicate a relative increase in the mass of one tissue in relation to another, in particular, an increase in muscle tissue relative to other tissues (e.g., adipose tissue). Growth further relates to nutritional status and disease resistance wherein improvement of nutritional status and/or increase in disease resistance is also indicative of improved growth performance.

In view of the foregoing, embodiments according to the present invention relate to methods of growing meat-type poultry, comprising feeding meat-type poultry an animal feed poultry diet wherein the feed further comprises keratinase and is added to the poultry diet in an amount effective to enhance the weight gain of the meat-type poultry. The poultry diet can be an animal feed which includes sources of protein, for example, soybean meal, fish meal, blood meal, poultry by-product (ground poultry offal), meat meal, wheat-meal, rapeseed, canola and combinations of the same. The animal feed further includes carbohydrates, for example, corn, oats, barley, sorghum, or combinations of the same that can be ground into a meal for use in the animal feed. Additionally, the animal feed can include vitamins, minerals, fat, antibiotics, and other substances or compounds as necessary or desired. Non-limiting examples of animal feed poultry diets include cereal-based feeds including cereals such as barley, corn, soya, wheat, triticale, and rye. Corn-soybean, wheat-soybean, and wheat-corn-soybean, sorghum-soybean, and corn-sorghum-soybean represent other non-limiting examples of suitable animal feeds according to the present invention. When the poultry diet is a corn-soybean meal feed, the corn-soybean meal feed comprises from about 60 to about 70% corn by weight and from about 20 to about 30% soybean by weight.

The poultry diet can further be categorized as a starter diet, a grower-type diet, or a finisher-type diet. The precise composition and physical characteristics of the animal feed, and thus the poultry diet, will depend upon the species for which the feed is intended, the age and/or weight of the animal, and the duration of feeding, and can be readily determined by those skilled in the art.

According to embodiments of the present invention, the methods of growing meat-type poultry do not require concurrently providing a specific keratin-containing substrate along with the keratinase; For example, in embodiments of the present invention, the keratinase can directly supplement a poultry diet as a feed additive in contrast to producing a hydrolyzed feather meal as described in Carter, 1998. Thus, the animal feed can be essentially free of keratin (e.g., not more than 1 or 2% by weight keratin.)

A keratinase suitable for practicing the present invention is obtained from *Bacillus licheniformis* strain PWD-1, which is described in U.S. Pat. Nos. 4,908,220 and 4,959,311 (the disclosures of all patent references cited herein are to be incorporated herein by reference). This bacterium was deposited with the American Type Culture Collection (ATCC) in Rockville, Md., USA in accordance with the Budapest Treaty on Mar. 23, 1988, and assigned ATCC Accession No. 53757. Other keratinases that can be used to practice the present invention are available from a variety of bacterial sources, such as *Streptomyces fradiae*. See generally U.S. Pat. No. 2,988,487 to Nickerson; See also Goktan, D., "Decomposition Rates of Keratinous Material Used by Certain Microorganisms," (Abstract No. 207369b), Microbial Biochem. 101, 333 (1984); Daniels, G., "The Digestion of Human Hair Keratin by *Microsporum Canis*," J. Gen. Microbiol. 8, 289 (1953); Koh, W. et al., "Keratinolytic Enzymes from *Aspergillus flavus* and *Aspergillus niger*," *Bacillus*. Aust. J. Biol. Sci. 274 (1959); Molyneaux, G. S., "The Digestion of Wool by a Keratinolytic *Bacillus*," Aust. J. Biol. Sci. 274 (1959); Noval, J. and Nickerson, W., "Decomposition of Native Keratin by *Streptomyces Fradiae*," J. Bacteriol, 77, 251 (1959); Kapica, L. and Blank, F., "Growth of *Candida Parapsilosis* with Keratin as Sole Source of Nitrogen," Dermatologica 117, 433 (1958); Kapica, L. and Blank, F., "Growth of *Albicans* on Keratin as Sole Source of Nitrogen," Dermatologica 115, 81 (1957).

Keratinase for practicing the present invention can be obtained by growing a host cell which contains nucleic acid sequences encoding a keratinase, under conditions which permit expression of the encoded keratinase, filtering the medium to remove the cells and collecting and concentrating the remaining supernatant by ultrafiltration to obtain the keratinase. Beneficiary co-factor(s) can also be obtained.

While strains of *B. licheniformis* are exemplified herein, it is contemplated that other eukaryotic and prokaryotic microbes containing nucleic acid sequences encoding a keratinase may also be useful in producing an animal feed supplement of the present invention. Eukaryotic and prokaryotic microbes containing nucleic acid sequences encoding a keratinase may include those which naturally produce the enzyme as well as strains genetically modified to express keratinase. In general, recombinant production of a protein may require incorporation of nucleic acid sequences encoding said protein into a recombinant expression vector in a form suitable for expression of the protein in a host cell. A suitable form for expression provides that the recombinant expression vector includes one or more regulatory sequences operatively-linked to the nucleic acids encoding the a keratinase protein in a manner which allows for transcription of the nucleic acids into mRNA and translation of the mRNA into the protein. Regulatory sequences may include promoters, enhancers and other expression control elements (e.g., polyadenylation signals). Such regulatory sequences are known to those skilled in the art and are described in Goeddel D. D., ed., Gene Expression Technology, Academic Press, San Diego, Calif. (1991). It should be understood that the design of the expression vector may depend on such factors as the choice of the host cell to be transfected and/or the level of expression required. Nucleic acid sequences or expression vectors harboring nucleic acid sequences encoding a keratinase protein may be introduced into a host cell, which may be of eukaryotic or prokaryotic origin, by standard techniques for transforming cells. Suitable methods for transforming host cells may be found in Sambrook, et al. (Molecular Cloning: A Laboratory Manual, 3rd Edition, Cold Spring Harbor Laboratory Press (2000)) and other laboratory manuals. The number of host cells transformed with a nucleic acid sequence encoding a keratinase protein will depend, at least in part, upon the type of recombinant expression vector used and the type of transformation technique used. Nucleic acids may be introduced into a host cell transiently, or more typically, for long-term expression of a keratinase protein the nucleic acid sequence is stably integrated into the genome of the host cell or remains as a stable episome in the host cell. Once produced, a keratinase protein may be recovered from culture medium as a secreted polypeptide, although it also may be recovered from host cell lysates when directly expressed without a secretory signal.

Eukaryotic microbes such as yeast cultures may be transformed with vectors carrying nucleic acid sequences encoding a keratinase, See, e.g., U.S. Pat. No. 4,745,057. *Saccharomyces cerevlsiae* is the most commonly used among lower eukaryotic host microorganisms, although a number of other strains are commonly available. Yeast vectors may contain an origin of replication from the 2 micron yeast plasmid or an autonomously replicating sequence (ARS), a promoter, DNA encoding a keratinase such as that provided in U.S. Pat. No. 5,712,147, sequences for polyadenylation, and transcription termination, and a selection gene. An exemplary plasmid is YRp7, (Stinchcomb, et al. (1979) *Nature* 282:39; Kingsman, et al. (1979) *Gene* 7:141; Tschemper, et al. (1980) *Gene* 10:157). Suitable promoting sequences in yeast vectors include the promoters for metallothionein, 3-phosphoglycerate kinase (Hitzeman, et al. (1980) *J. Biol. Chem.* 255:2073) or other glycolytic enzymes (Hess, et al. (1968) *J Adv. Enzyme Reg.* 7:149; Holland, et al. (1978) *Biochemistry* 17:4900). Suitable vectors and promoters for use in yeast expression are further described in EPO Publication. No. 73,657. Further, fungal strains such as of *Trichoderma* (e.g., *T. longibrachialum, T. reesei or T. viride*) are particularly useful in expressing secreted enzymes.

Prokaryote host cells which may be used to produce a keratinase include gram negative or gram-positive organisms, for example *Escherichia coli* (*E. coli*) or Bacilli. Exemplary host cells are *E. coli* W3110 (ATCC 27,325), *E. coli* 13, *E. coli* X1776 (ATCC 31,537), *E. coli* 294 (ATCC 31,446). A broad variety of suitable prokaryotic and microbial vectors are available. *E. coli* is typically transformed using pBR322. Promoters most commonly used in recombinant microbial expression vectors include the beta-lactamase (penicillinase) and lactose promoter systems (Chang, et al, (1978) *Nature* 275:615; Goeddel, et al. (1979) *Nature* 281:544), a tryptophan (trp) promoter system (Goeddel, et al. (1980) *Nucleic Acids Res.* 8:4057; EPO Publication No. 36,776) and the tac promoter (De Boer, et al. (1983) *Proc. Natl. Acad. Sci. USA* 80:21). The promoter and Shine-Delgamo sequence (for prokaryotic host expression) are operable linked to the DNA encoding the keratinase, i.e., they are positioned so as to promote transcription of keratinase messenger RNA from the DNA. A species of *Bacillus* is preferably used in the production of a keratinase. Recombinant expression vectors for *Bacillus* are well known to those of skill in the art. *Bacillus* strains can be *B. alkalophilus, B. amyloliquefaciens, B. brevis, B. circulans, B. coagulans, B. firmus, B. lautus, B. lentus, B. licheniformis, B. megaterium, B. pumilus, B. stearothermophilus, B, subtilis,* and *B. thuringiensis*. In a preferred embodiment, strains of *B. licheniformis* are utilized. In some embodiments, *B. licheniformis* strains T399D or PWD-1 are utilized.

As provided herein, a keratinase enzyme may be produced by culturing a host cell as described above under conditions that permit expression of the encoded keratinase, and collecting the expressed keratinase. The host cell may be cultured under conditions in which the cell grows, and then cultured under conditions which cause the expression of the encoded keratinase, or the cells may be caused to grow and express the encoded keratinase at the same time. Such conditions are well known to one of skill in the art and may vary with the host cell and the amount of enzyme expression level desired.

In some embodiments, the medium used to cultivate the transformed host cells may be any medium suitable for keratinase production. The keratinase is recovered from the medium by conventional techniques including separation of the cells from the medium by centrifugation, or filtration, and concentration of the proteins in the supernatant or filtrate by ultrafiltration or evaporation followed by drying via lyophilization or spray-drying.

Alternatively, the culture supernatant may be spray-dried or lyophilized after separation without being concentrated.

The keratinase should be present in an amount at least sufficient to achieve the intended effect, but the upper limit to the amount of keratinase can be determined based upon achieving the intended effect. In some embodiments, the animal feed comprises from about 0.01% to about 20% *Bacillus licheniformis* PWD-1 keratinase by weight. Additionally, keratinases used in practicing the present invention can be in crude form or in pure form. Keratinases in crude form can be prepared, for example, by separating bacterial cells which produce the keratinase from their liquid growth media, the liquid growth media comprising crude keratinase. Alternatively, the cells can be lysed (chemically or physically) in a liquid growth media to produce a crude, cell free extract. Other means of preparing such an extract will be apparent to persons skilled in the art. The crude keratinase can be included in the feed in any form compatible therewith, such as in an aqueous form or in lyophilized form. In some embodiments, the crude keratinase is in the lyophilized form.

Pure (or substantially pure) keratinases can be obtained by separating the crude keratinase described above into its individual constituents, in accordance with known techniques. See generally W. Jakoby, Ed., Enzyme purification and Related Techniques, Methods in Enzymology, vol, 22 (1971) and vol. 104, pt. C (1984), Academic Press, NY. Numerous suitable separation procedures, such as column chromatography, are known to persons skilled in the art. The individual constituent proteins can be screened for their ability to degrade keratinaceous material, and that constituent which best degrades keratinaceous material comprises the keratinase. Like the crude keratinase, the pure keratinase can be employed in any suitable form, including aqueous form and lyophilized form.

Embodiments of the present invention further relate to methods of improving the efficiency of feed utilization of an animal feed in meat-type poultry comprising feeding meat-type poultry an animal feed poultry diet wherein the feed further comprises keratinase in an amount effective to improve the efficiency of feed utilization of an animal feed provided to meat-type poultry. The animal feed can include the animal feeds as described above and, in particular embodiments can be corn-soybean meal. The keratinase can include keratinases as described above including, but not limited to, *Bacillus licheniformis* PWD-1 keratinase. As described above, the keratinase can be a crude extract or pure form enzyme.

Improving the efficiency of feed utilization refers to a reduction in the Feed Conversion Ratio (FCR) as compared with that which would otherwise occur without implementation of the methods and/or administration of the compositions of the present invention. The FCR is the ratio of the amount of feed consumed relative to the weight gain of an animal. In one embodiment of the present invention, the improved efficiency of feed utilization can occur by increasing gastrointestinal nutrient absorption without a concomitant increase in intestinal energy expenditure. In another embodiment of the present invention, the improved efficiency of feed utilization can occur by increasing the digestibility of the animal feed. In another embodiment of the present invention, the improved efficiency of feed utilization can occur by decreasing the viscosity of the animal feed. In particular embodiments, the present invention relates to methods of increasing the digestibility of an animal feed in a meat-type poultry comprising feeding meat-type poultry an animal feed poultry diet wherein the feed further comprises *Bacillus licheniformis* PWD-1 keratinase in an amount effective to increase the digestibility of an animal feed in meat-type poultry. The animal feed can include the animal feeds as described above and, in particular embodiments, can be corn-soybean meal. The keratinase can include keratinases as described above including, but not limited to, *Bacillus licheniformis* PWD-1 keratinase. As described above, the keratinase can be a crude extract or pure form enzyme. Increasing the digestibility of an animal feed refers to increasing the availability of nutrients absorbed from the animal's gut without a concurrent increase in feed intake or nutrient ingestion. In some embodiments of the present invention, the viscosity of materials present in the animal's gut or digesta viscosity is reduced. In other embodiments, the entrapment of nutrients rendering them nutritionally unavailable to the animal is reduced.

In other embodiments, the present invention relates to methods of reducing mortality in meat-type poultry comprising feeding meat-type poultry an animal feed poultry diet wherein the feed further comprises a keratinase in an amount effective to reduce the mortality of meat-type poultry, for example immature birds, and more specifically, broiler chicks. The animal feed can include the animal feeds as described above and, in particular embodiments, can be corn-soybean meal. The keratinase can include keratinases as described above including, but not limited to, *Bacillus licheniformis* PWD-1 keratinase. As described above, the keratinase can be a crude extract or pure form enzyme. Reducing mortality refers to increasing the survivability or decreasing the death rate in animals after birth or hatch as compared with that which would otherwise occur in the absence of implementation of the methods and/or administration of the compositions of the present invention. Mortality can be from any cause, in particular, stress, stunting, "starveouts", and disease. In some embodiments, the present invention reduces mortality in immature birds. In other embodiments, the birds are about 1, 2, 3, 4, 5, 6, 7, 8, 9, 10, 11, 12, 13, 14, 15, 16, 17, 18, 19, 20, 21, 22, 23, 24, 25, 26, 27, 28, 29, 31, 32, 33, 34, or 35 days old, preferably about 1 to about 21 days old, and more preferably about 1 to about 5 days old.

In some embodiments, the present invention relates to an animal feed comprising protein, carbohydrate, and keratinase as the major components. The keratinase is a major component supplementing the animal feed. The animal feed can include the animal feeds as described above and, in particular embodiments, can be corn-soybean meal. The keratinase can include keratinases as described above to including, but not limited to, *Bacillus licheniformis* PWD-1 keratinase. As described above, the keratinase can be a crude extract or pure form enzyme.

The animal feed supplement provided by the present invention can be mixed directly with the animal feed, such as one comprising barley, to prepare the final feed. Alternatively, the animal feed supplement can be mixed with one or more other animal feed supplements such as a vitamin animal feed supplement, a mineral animal feed supplement and an amino acid animal feed supplement. The resulting animal feed supplement including several different types of components may then be mixed in an appropriate amount with the animal feed.

The animal feed of the present invention comprises keratinase in an amount at least sufficient to achieve the intended effect, wherein the upper limit to the amount of keratinase can be determined based upon achieving the intended effect. Intended effects include, but are not limited to, enhancing animal growth performance, such as weight gain, improving the efficiency of feed utilization, increasing feed digestibility, and decreasing mortality. The animal feed supplement added to the animal feed can comprise up to 100% keratinase by weight. The animal feed comprising the supplement comprises from about 5% to about 25% keratinase by weight. In some embodiments, the keratinase is Bacillus licheniformis PWD-1 keratinase.

Any animal is a suitable subject for the present invention, including cows, sheep, pigs, cats, dogs, ferrets, and avians, however, the present invention is preferably employed with monogastric animals. Suitable subjects can be of any age range including neonatal animals, developing animals, and mature animals. In some embodiments, the suitable subject can be an avian, preferably a chicken, and more preferably a broiler chick. In other embodiments the suitable subject can be a chicken. In still other embodiments, the suitable subject can be an immature, developing, or mature bird. In other embodiments, the suitable subject can be a chicken that is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, or 65 days old, or within any range of these numbers. Thus, the present invention provides a variety of different feeds, including pet feed, poultry feed, and pig feed.

The animal feed supplement of the present invention can also enable a conventional animal feed to be modified by reducing its energy, and/or protein, and/or amino acid content while simultaneously maintaining the same nutritional levels of energy, protein, and amino acids available to the animal. Consequently, the amounts of costly energy and protein supplements typically included in an animal feed can be reduced as compared to conventional feeds.

The following Examples are provided to illustrate the present invention, and should not be construed as limiting thereof.

EXAMPLE 1

Production of Keratinase from Recombinant B. Licheniformis PWD-1 Strain

A fermentation scale-up strategy was designed for the production of keratinase, using the wild-type B. licheniformis strain PWD-1, Flask Culture in LB Medium. Flask culture was carried out in Luria-Bertani (LB) medium that was prepared according to the manufacturer's specification, containing: 1.0 L of distilled water, 15 g BACTO® agar, 10 g NaCl, 10 g BACTO® tryptone, and 5.0 g yeast extract. B. licheniformis strain PWD-1 was streaked from a glycerol stock onto an LB plate and grown at 50° C. for 8-12 hours. A single colony of B. licheniformis strain PWD-1 was then transferred from the LB plate into a flask that contained 500 ml LB medium, and grown at 50° C. for 6 hours.

Seed Cultures. Seed cultures for B. licheniformis strain PWD-1 were conducted in a medium containing: 0.7 g/L $KH_2PO_4$, 1.4 g/L $K_2HPO_4$, 0.1 g/L $MgSO_4.7H_2O$, 10 g/L defatted soy flour, and 0.1 g/L antifoaming agent. The initial pH of the seed culture was adjusted to 7.0 by adding 1M HCl or NaOH.

The 500 ml flask culture was transferred into a first stage seed fermentor of about 10 L to 20 L that contained the seed culture medium, and was grown therein at 50° C. for 8-12 hours to reach 2.5% to 5% inoculum size. The first stage seed culture was then transferred to a second stage seed fermentor of 100 L, 250 L or 800 L, and was grown therein at 50° C. for 8 hours and then shifted to 37° C.

For the seed culture, the cell density reached at least $3\times10^8$ CFU/mL at about 8 or 10 hours of the culture process.

Production Media. The production culture medium used for B. licheniformis strain PWD-1 contained 0.7 g/L $KH_2PO_4$, 1.4 g/L $K_2HPO_4$, 0.1 g/L $MgSO_4.7H_2O$, 10 g/L defatted soy flour and 0.1 g/L antifoaming agent. The initial pH of the production culture was adjusted to 7.0 by adding 1M HCl or NaOH.

The second stage seed culture was transferred to a production fermentor that contained the production culture medium for final stage culturing. The final stage culture was carried out at 50° C. for 8 hours, reaching a total culturing time of about 24 to 30 hours before harvesting.

During the above culturing steps, the initial pH of the culture medium was adjusted to 7.0, but no pH control during the culture process was provided. The optimal level of dissolved oxygen was about 20% for B. licheniformis strain PWD-1. The inoculum size was about 2.5 to 5%, and the inoculum age was about 8-12 hours.

For the production culture, the peak cell density reached $1.2\times10^9$ CFU/mL at about 20 or 24 hours of the culture process. The peak enzyme activity, as measured by azocasein assay, reached 35-40 $A_{450}$ per mL at about 24 to 30 hours of the culture process. The pH value of the production culture medium changed from 7.0 to 8.3, but the enzyme activity and productivity stayed at high levels, which indicated that no pH control was necessary.

Recovery and Downstream Processing. The enzyme activity in the production culture was checked before harvesting. The culture supernatant was separated from the cell mass via centrifuge, and then concentrated via ultrafiltration or evaporation. The concentrated liquid enzyme was then spray-dried.

Alternatively, the culture supernatant was directly spray-dried after separation from the cell mass, without being concentrated.

Enzyme Yield and Enzyme Activity. For 100 L production culture, the enzyme activity measured by azocasein assay before harvesting was 3,000 to 3,500 U/mL, and the cell number was $1.3\times10^9$ CFU/mL. The total dry weight of the 100 L production culture was 9.12 g/L, including 2.15 g/L insoluble dry weight and 6.88 g/L soluble dry weight.

The crude enzyme yield was about 1.75-2.0 g/L. The crude enzyme was prepared by concentration of the fermentation supernatant via Pellicon filtration with a 5 kDa molecular weight cut-off, and then freeze dried. The enzyme activity of the crude dry enzyme was about 1,000,000 to about 1,400,000 U/g, as measured by the azocasein assay. The total protein content of the crude dry enzyme was about 30-36%, of which approximately 14-20% consisted of pure keratinase.

EXAMPLE 2

Production of Keratinase from Recombinant B. licheniformis T399D Strain

A fermentation scale-up strategy was designed for the production of keratinase, using a recombinant Bacillus licheniformis T399D strain (hereinafter the "Bacillus licheniformis strain T1").

Flask Culture in LB Medium. Flask culture was carried out in LB medium that was prepared according to the manufacturer's specification, containing: 1.0 L of distilled water, 15 g BACTO® agar, 10 g NaCl, 10 g BACTO® tryptone, and 5.0 g yeast extract. *B. licheniformis* strain T1 was streaked from a glycerol stock onto LB plates and grown at 37° C. for 18 hours. A single colony of *B. licheniformis* strain T1 was then transferred from the LB plate into a flask that contained 500 mL LB medium, and grown at 37° C. for 6 hours. Cell growth was monitored by measuring the optical density at 660 nm (Beckman DU Series 660 Spectrophotometer, Fullerton, Calif.), After 6 hours of growth, the $OD_{660}$ measured above 1.0.

Seed Cultures. Seed cultures for B, *licheniformis* strain T1 were grown in a medium containing: 0.7 g/L $KH_2PO_4$, 1.4 g/L $K_2HPO_4$, 0.1 g/L $MgSO_4.7H_2O$, 10 g/L defatted soy flour, and 0.1 g/L antifoaming agent. The initial pH of the seed culture was adjusted to 7.0 by adding 1 M HCl or NaOH.

The 500 mL flask culture was transferred into a first stage seed fermentor of about 10 L to 20 L that contained the seed culture medium, and was grown therein at 37° C. for 8 hours to reach 2.5% to 5% inoculum size. The first stage seed culture was then transferred to a second stage seed fermentor of 100 L, 250 L or 800 L, and was grown therein at 37° C. for 8 hours.

Production Media. The production culture medium used for B, *licheniformis* strain T1 contained 0.7 g/L $KH_2PO_4$, 1,4 g/L $K_2HPO_4$, 0.1 g/L $MgSO_4.7H_2O$, 13 g/L defatted soy flour, 40 g/L starch, 13 g/L feather meal, and 0.1 g/L antifoaming agent, The initial pH of the production culture was adjusted to 7.0 by adding 1 M HCl or NaOH.

The second stage seed culture was transferred to a production fermentor that contained the production culture medium for final stage culturing. The final stage culture was carried out at 37° C. for 48 hours before harvesting.

During the above culturing steps, the initial pH of the culture medium was adjusted to 7.0, but no pH control was provided. The optimal level of dissolved oxygen was about 30% for *B. licheniformis* strain T1. The inoculum size was about 2.5 to 5%, and the inoculum age was about 12 hours.

Recovery and Downstream Processing. Enzyme activity in the production culture was checked before harvesting. The culture supernatant was separated from the cell mass via centrifugation, and then concentrated via ultrafiltration or evaporation. The concentrated liquid enzyme was then spray-dried.

Alternatively, the culture supernatant was directly spray-dried after separation from the cell mass, without being concentrated.

Enzyme Yield and Enzyme Activity. For 100 L production culture, the enzyme activity measured by azocasein assay before harvesting was 30,000 to 35,000 U/mL, and the cell number was $6 \times 10^9$ CFU/mL. The total dry weight of the 100 L production culture was 40 g/L, including 15 g/L insoluble dry weight and 25 g/L soluble dry weight.

The crude enzyme yield from the directly dried culture supernatant was 20 g/L, while the crude enzyme yield from a culture concentrate, as obtained via Pellicon filtration with a 10 kDa molecular weight cut-off, was 16 g/L. The enzyme activity of the crude dry enzyme was greater than 1,000,000 U/g, as measured by the azocasein assay.

EXAMPLE 3

Materials and Methods of Supplementation of Poultry Feed with Keratinase

Birds and Housing. Three experiments were conducted. In each experiment, 192 day-old broiler chicks were weighed and randomly assigned to 24 cage-pens in a completely randomized design to two Alternate Design batteries (Wilveco, Billerica, Mass.). Birds were weighed, wing-banded and introduced to the experimental treatments at five (experiments one and two) or one (experiment three) day of age. Each treatment was replicated five times with eight birds per pen except for the control treatment that was replicated four times with eight birds per pen. The birds were housed in a room with controlled temperature, ventilation, and lighting (24 hours/day), During the experimental period the birds were feed ad libitum in trough feeders and water by nipple drinkers.

The PWD-1 Keratinase Enzyme. The enzyme, PWD-1 keratinase was produced with a 150-L fennentor using standard methods (Wang and Shih (1998) *J. Indust, Microb. Biotech,* 22:608-616). Briefly, *Bacillus licheniformis* PWD-1 (Williams, et al. (1990) supra) was grown in the fermentor at 50° C. for 48 hours. The cell-free media were concentrated by membrane ultrafiltration and dried by a freeze-dryer. Typically, the yield of the crude enzyme was 2.0 g/L. The crude keratinase had an activity of 300,000 U/g as measured by the hydrolysis of azo-keratin (Lin, et al. (1992) supra).

Dietary Treatments. All diets were formulated using least-cost linear programming software and are presented in Table 1.

TABLE 1

| Ingredient | Dietary treatment | | |
|---|---|---|---|
| | High protein[1] | Control[2] | Low Protein |
| Corn | 49.60 | 59.00 | 49.00 |
| Soybean meal, 48% CP | 41.44 | 32.00 | 26.60 |
| Limestone | 1.32 | 1.40 | 1.32 |
| Dical phosphate | 1.75 | 1.70 | 1.82 |
| Poultry fat | 5.34 | 5.00 | 4.20 |
| DL-Methionine | 0.15 | 0.16 | 0.13 |
| Salt | 0.40 | 0.50 | 0.42 |
| Choline chloride | 0.10 | 0.10 | 0.08 |
| Minerals[3] (TM-90) | 0.12 | 0.12 | 0.10 |
| Vitamins[4] (NCSU-90) | 0.07 | 0.07 | 0.06 |
| Selenium premix[5] | 0.07 | 0.07 | 0.06 |
| Sodium Bicarbonate | 0.10 | 0.10 | 0.08 |
| Starch, corn | 0 | 0 | 16.60 |
| Total (kg) | 100.46 | 100.22 | 100.47 |

TABLE 1-continued

|  | Analysis[6] | % NRC | Analysis | % NRC | Analysis | % NRC |
|---|---|---|---|---|---|---|
| Crude protein, % | 25.00 | 108.70 | 20.23 | 88.00 | 16.80 | 72.90 |
| ME, kcal/kg | 3.050 | 95.31 | 3.201 | 100.00 | 3.257 | 101.80 |
| Met + Cys, % | 0.933 | 103.67 | 0.85 | 99.00 | 0.70 | 77.90 |
| Lysine, % | 1.437 | 130.60 | 1.17 | 106.30 | 0.97 | 88.10 |
| Calcium, % | 1.00 | 100.00 | 1.03 | 103.30 | 1.01 | 100.10 |
| Available Phosphate, % | 0.45 | 100.00 | 0.45 | 100.70 | 0.45 | 100.70 |

[1]Provided to birds ad libitum for the first 5 days of age in experiment three only.
[2]Provided to birds ad libitum for the first 5 days of age in experiments one and two, In all experiments, birds on the control treatment continued to receive the same diet after the first 5 days of age while other birds were subjected to corresponding treatments.
[3]The mineral premix was obtained from Eastern Minerals, Inc., Henderson, NC and provided the following (per kg of diet): 120 mg Zn from $ZnSO_4$; 120 mg Mn from $MnSO_4$; 80 mg Fe from $FeSO_4C5H_2O$; 10 mg Cu from $CuSO_4$; 2.5 mg I from $CaIO_4$; and 1 mg Co from $CoSO_4$.
[4]The vitamin premix was obtained from Roche, Nutley, NJ and provided the following (per kg of diet): 13,200 IU vitamin A; 4,000 ICU vitamin D; 66 IU vitamin E; 39.6 Fg vitamin $B_{12}$; 13.2 mg riboflavin; 110 mg niacin; 22 mg d-pantothenate; 0.4 mg vitamin K; 2.2 mg folic acid; 4.0 mg thiamin; 7.9 mg pyridoxine; 0.253 mg biotin; 100 mg ethoxyquin.
[5]The selenium premix provided 0.2 mg Se/kg diet as $Na_2SeO_3$.
[6]Calculated analysis.

All feed was fed in mash form throughout the experiments. Birds received a basal diet at one day of age and were subsequently switched to the corresponding experimental diets at five days of age. In experiment one, the basal diet fed for the first five days was about 93% of the National Research Council's (NRC) recommendations for crude protein ((1994) supra) but provided 100% for essential amino acids, energy, and calcium and phosphorus contents. In experiments two and three, the basal diet fed for the first 5 days was about 95% of the NRC recommendations ((1994) supra) for energy and 100% of the calcium and phosphorus but provided 105% crude protein content. Subsequently, a pen of broiler chicks was subjected to one of five dietary treatments through to the end of each experiment (21 days in experiments one and three, 26 days in experiment two). The five dietary treatments in experiment one and two were: 1) unsupplemented control diet (C, 21,39% crude protein); 2) low protein diet (LP, 18% crude protein); 3) low protein diet supplemented with 0.05% (wt/wt) enzyme preparation (LP+0.05 E); 4) low protein diet supplemented with 0.10% (wt/wt) enzyme preparation (LP+0.10 E); and 5) low protein diet supplemented with 0.15% (wt/wt) enzyme preparation (LP+0.15 E). The control diet was the same basal diet fed to the birds for the first five days of age in experiment one. Birds on treatment one continued to receive the same diet after five days of age, while the rest of the treatments were switched to the experimental diets at five days of age. The dietary treatments in experiment three were: 1) unsupplemented control (C, 21.39% crude protein); 2) control diet supplemented with 0.10% (wt/wt) enzyme preparation (C+0.10 E); 3) low protein diet (LP, 18% crude protein); 4) low protein diet supplemented with 0.10% (wt/wt) enzyme preparation (LP+0.10 E); and 5) same as treatment two but fed to birds starting at one day of age rather than five days of age.

The enzyme dosage was dissolved in 0.10 N sodium carbonate solution in a ratio of 1 gram enzyme/10 ml solution prior to feed application. Thereafter, the enzyme solution was sprayed on top of the feed using a spray bottle in a ratio of 10 ml enzyme preparation/kg diet and mixed using a small bowl mixer (The Hobart Manufacturing Company, Troy, Ohio).

Viscosity of Digestae. At the end of each experiment, all of the birds but two per pen were euthanized using $CO_2$ gas. The two remaining birds per pen were kept for the next day. Early the next day, feeders were removed from the pens to produce a 2-hour period with no access to feed. After the 2 hours, birds were once again allowed access to the feed ad libitum. An hour later, the birds were removed, two at a time, and were subsequently euthanized using $CO_2$ gas. Necropsy was carried out immediately after euthanization, and the jejunal contents were emptied into 1-ml Eppendorf tubes. Two samples were obtained per bird. The tubes were immediately centrifuged at 12,000×g for 5 minutes and immediately placed in ice until viscosity was measured using a commercial type viscometer (Brookfield Digital Viscometer, Model DV-II Version 2.0, Brookfield Engineering Laboratories, Inc., Stoughton, Mass.), Viscosity reading was conducted under conditions that avoided any bacterial growth in the solution.

Data Analysis. Body weights and feed consumption were recorded at 5-day intervals starting day one of age and through the end of each experiment. Feed conversion ratio (feed-to-weight gain), corrected for mortality and culls, was calculated. Mortality was recorded daily. Body weight, feed consumption, feed conversion ratio, and viscosity readings of each experiment were analyzed separately using one-way analysis of the general linear model procedures of SAS software (SAS Institute (1996) SAS/STAT User's Guide: Statistics. Release 6.11. SAS Institute, Inc., Cary, N.C.). The percentage data were subjected to ANOVA after arcsine square root percentage transformation. The means were separated using least significant difference. Statements of significance were based on $P<0.05$.

EXAMPLE 4

Supplementation of Poultry Feed with Keratinase: Experiment 1

Final body weight, cumulative feed consumption, and feed conversion ratios are presented in Table 2.

TABLE 2

| Treatment | Body Weight (g) | Feed Consumption (g) | Feed Conversion ratio |
|---|---|---|---|
| Control (C) | 709 ± 16 | 901[a] ± 26 | 1.56 ± 0.05 |
| Low protein (LP) | 668 ± 14 | 835[ab] ± 23 | 1.57 ± 0.04 |
| LP + 0.05 E | 691 ± 14 | 860[ab] ± 23 | 1.56 ± 0.04 |
| LP + 0.10 E | 700 ± 14 | 847[ab] ± 23 | 1.51 ± 0.04 |
| LP + 0.15 E | 677 ± 14 | 826[b] ± 23 | 1.54 ± 0.04 |

[a,b]Means within a column with differing superscripts differ significantly ($P < 0.05$) according to the least squares means function of SAS software (SAS Institute (1996) supra).
[1]Values represent means of four to five pens of eight broiler chicks per pen. Values represent means ± standard error of the mean.
[2]E = enzyme.

The enzyme treatments generally improved body weight with a probability value of P>0.05. The low protein+0.10% enzyme treatment had higher body weight than the low protein treatment (700 vs. 668 grams for low protein+0.10% enzyme vs, low protein, respectively, P=0.08). The low protein+0.10% enzyme treatment had the highest body weight among the enzyme treatments and was not different from the control treatment (700 vs. 709 grams for the low protein+0.10% enzyme vs, control, respectively).

There were no significant differences among the treatments in feed consumption except between the low protein+0.15% enzyme and the control treatment (826 vs. 901 grams for the low protein+0.15% enzyme vs. control, respectively, P<0.05). There were no significant differences in feed consumption among the enzyme treatment groups.

There was only one dead bird throughout the whole experiment. The weight of this dead bird and the culls were included in the calculation of feed conversion ratio, which is presented in Table 2. Dietary enzyme supplementation had marginal effects on feed conversion ratio. On a cumulative basis, the low protein+0.10% enzyme treatment had the lowest feed conversion ratio (1.51 vs. 1.57 for the low protein+0.10% enzyme vs. low protein, respectively, P>0.05).

The results of the first experiment revealed a trend in the response for the to enzyme treatment. To further analyze the positive effect of the enzyme for a longer time, a second experiment was conducted growing the birds 5 more days (to 26 days of age).

EXAMPLE 5

Supplementation of Poultry Feed with Keratinases:
Experiment 2

This experiment was a repeat of experiment 1 except that birds were grown 5 more days (to 26 days of age). Final body weight, cumulative feed consumption, and feed conversion ratio are presented in Table 3.

TABLE 3

| Treatment | Body Weight (g) | Feed Consumption (g) | Feed Conversion ratio |
|---|---|---|---|
| Control (C) | $1089^a \pm 15$ | $1717^c \pm 16$ | $1.83^a \pm 0.04$ |
| Low protein (LP) | $964^c \pm 13$ | $1734^b \pm 14$ | $2.14^c \pm 0.04$ |
| LP + 0.05 E | $1019^b \pm 13$ | $1796^a \pm 14$ | $2.08^{bc} \pm 0.04$ |
| LP + 0.10 E | $1025^b \pm 13$ | $1764^{ab} \pm 14$ | $2.02^b \pm 0.04$ |
| LP + 0.15 E | $1032^b \pm 13$ | $1794^a \pm 14$ | $2.04^{bc} \pm 0.04$ |

$^{a,b,c}$Means within a column with differing superscripts differ significantly (P < 0.05) according to the least squares means function of SAS software (SAS Institute (1996) supra).
[1]Values represent means of four to five pens of eight broiler chicks per pen. Values represent means ± standard error of the mean.
[2]E = enzyme.

There was an improvement in body weight (P<0.05) upon supplementing the low protein diet with all three levels of the enzyme at 26 days of age. The low protein+0.10% enzyme treatment and the low protein+0.15% enzyme treatment gave the highest body weight improvement (1,032 and 1,025 vs. 964 grams for the low protein+0.15% enzyme and low protein+0.10 vs, low protein, respectively, P<0.05). However, all the enzyme treatments had lower (P<0.05) body weight than the control treatment (1,032, 1,025, and 1,016 vs. 1,089 grams for the low protein+0.15% enzyme, low protein+0.10% enzyme and the low protein+0.05% enzyme vs. control, respectively).

All birds receiving the low protein diet consumed more feed than the control group (P<0.05). Enzyme treatment groups also consumed more feed than the low protein diet (P<0.05; Table 2). There were no significant differences in feed consumption among the enzyme treatments. Enzyme supplementation at 0.05 and to 0.15% levels resulted in numerically better feed conversion ratios than the low protein treatment, while the low protein+0.10% enzyme treatment showed significantly<0.05) a better feed conversion ratio than the low protein treatment (2.02 vs. 2.14 for the low protein+0.10% enzyme vs. low protein, respectively). In this experiment, supplementing the low protein diet with enzyme did not improve the performance of the chicks to a level equivalent to that of the control diet. However, supplementing the low protein diet with the 0.10% enzyme (wt/wt) level did (P<0.05) improve the performance of chicks over that of the low protein diet.

The birds in both experiments 1 and 2 were provided the control diet for the first 5 days of age prior to being subjected to the treatment diets. Although the control diet provided adequate energy, calcium and phosphorus, and essential amino acids, it provided only 93% of the NRC ((1994) supra) crude protein recommendation, which made it marginally adequate and sensitive to protease supplementation.

EXAMPLE 6

Supplementation of Poultry Feed with Keratinase:
Experiment 3

In experiment 3, birds were provided a high protein prestarter diet providing 105% of the NRC ((1994) supra) recommendation for crude protein and slightly higher than requirements for all other nutrients except for energy (95% of NRC recommendations; Table 1). Experiment 3 was conducted to determine whether or not the enzyme would continue to exert its effect even after the chicks had received adequate nutrient requirements.

In this experiment, only one level of the enzyme was used (0.10% wt/wt). However, two new treatments were introduced to test the enzyme's ability to exert an effect upon supplementation to marginally adequate broiler starter diets. The two new treatments consisted of supplementing the same control diet (21.39% crude protein) used in experiments 1 and 2 with 0.10% enzyme (wt/wt) and introducing the treated feed to the chicks either at five days (treatment 2) or one day (treatment 5) of age. This provided information whether enzyme supplementation at one day of age would have any further improvements in performance.

Final body weight, cumulative feed consumption, and feed conversion ratio are presented in Table 4.

TABLE 4

| Treatment | Body Weight (g) | Feed Consumption (g) | Feed Conversion ratio |
|---|---|---|---|
| Control (C) | $695^b \pm 14$ | $974^b \pm 18$ | $1.49^{ab} \pm 0.03$ |
| C + 0.10 E | $767^a \pm 13$ | $1046^a \pm 16$ | $1.45^a \pm 0.03$ |
| Low protein (LP) | $651^c \pm 13$ | $1043^a \pm 16$ | $1.71^c \pm 0.03$ |
| LP + 0.10% E | $679^{bc} \pm 13$ | $978^b \pm 16$ | $1.53^b \pm 0.03$ |
| C + 0.10% E[3] | $764^a \pm 13$ | $1022^{ab} \pm 16$ | $1.42^a \pm 0.03$ |

$^{a,b,c}$Means within a column with differing superscripts differ significantly (P < 0.05) according to the least squares means function of SAS software (SAS Institute (1996) supra).
[1]Values represent means of four to five pens of eight broiler chicks per pen. Values represent means ± standard error of the mean.
[2]E = enzyme.
[3]The enzyme was added at one day of age in this treatment. All others were added at five days of age.

Although the data in Table 2, Table 3, and Table 4 show only the final body weight numbers of the birds in the different experiments, the birds were weighed every 5 days in each of the experiments. Looking at the 5-day interval numbers for this experiment, it was clear that supplementing the low protein diet with the enzyme in experiment 3 showed similar effect on body weight gain to those of experiments 1 and 2. Supplementing the low protein diet with the enzyme increased the 21-day body weight of the birds, but the effect could not be detected at P<0.05 (679 vs. 651 grams for the low protein+0.10% enzyme vs. low protein, respectively, P>0.05). However, supplementing the control diet with the enzyme (control+0.10% enzyme preparation, treatments 2 and 5) showed higher body weight than the control treatment (767 and 764 vs. 695 grams for treatments 2 and 5 vs, control, respectively, P<0.05). Unexpectedly, supplementation of the control diet with the enzyme showed significantly higher improvements in body weight than when the low protein diet was supplemented with the enzyme whether the enzyme was supplemented at one or five days of age (Table 4). This may have been due to the higher protein and/or amino acids content of the control diet vs. the low protein diet. Keratinase is a broad-spectrum protease enzyme that attacks proteins of different sources and breaks them down into smaller polypeptide components. These polypeptides become easier to degrade by the digestive enzymes in the lumen of the intestines. Higher crude protein and/or amino acids content of the diet (in this case the control diet) means higher substrate content for the enzyme to work on releasing more protein components and making it more available to the young chick which, in turn, will be reflected in higher body weight gain.

EXAMPLE 7

Supplementation of Poultry Feed with Keratinase: Digestae Viscosity

The viscosity readings (mPas) of the jejunal contents of 22-day-old (experiments 1 and 2) and 27-day-old (experiment 3) broiler chicks from all three experiments are presented in Table 5.

TABLE 5

| Treatment | Experiment 1 | Experiment 2 | Experiment 3 |
|---|---|---|---|
| Control (C) | $3.65^b \pm 0.42$ | $2.31^b \pm 0.15$ | $2.55^{ab} \pm 0.17$ |
| C + 0.10 E | — | — | $2.18^b \pm 0.15$ |
| C + 0.10 E$^3$ | — | — | $1.99^b \pm 0.15$ |
| Low protein (LP) | $3.59^b \pm 0.38$ | $2.36^{ab} \pm 0.14$ | $2.97^a \pm 0.15$ |
| LP + 0.05 E | $2.98^{ab} \pm 0.38$ | $2.78^a \pm 0.14$ | — |
| LP + 0.10 E | $2.88^{ab} \pm 0.38$ | $2.21^{bc} \pm 0.14$ | $2.20^b \pm 0.15$ |
| LP + 0.15 E | $2.27^a \pm 0.38$ | $1.98^c \pm 0.14$ | — |

$^{a,b,c}$Means within a column with differing superscripts differ significantly (P < 0.05) according to the least squares means function of SAS software (SAS Institute (1996) supra).
$^1$Values represent means of four to five pens (16-20 numbers). Values represent means ± standard error of the mean.
$^2$E = enzyme.
$^3$The enzyme was added at one day of age in this treatment. All others were added at five days of age.

Supplementing both the low protein and the control diets in all the experiments with keratinase reduced the viscosity of jejunal contents. The reduction was directly proportional to the level of enzyme supplementation. Supplementing the low protein diet with 0.15% enzyme (low protein+0.15% enzyme) reduced the viscosity of the jejunal contents in experiments 1 and 2 (2.27 and 1.98 mPas vs. 3.59 and 2.36 mPas for low protein+0.15% enzyme vs. low protein in experiments 1 and 2, respectively, P<0.05). The low protein+0.15% enzyme treatment also had a lower jejunal viscosity when compared to the control treatment (2.27 and 1.98 mPas vs. 3.65 and 2.31 mPas for the low protein+0.0.15% enzyme vs. control in experiments 1 and 2, respectively, P<0.05).

When supplementing the control diet with keratinase at 5 days of age, jejunal viscosity was also reduced (2.18 mPas vs. 2.55 mPas for the control+0.10% enzyme [experiment 3, treatment 2] vs. control, respectively, P>0.05). However, the reduction was significant only when the diet supplemented with the enzyme starting at 1 day of age (1.99 mPas vs. 2.55 mPas for the control+0.10% enzyme [experiment 3, treatment 5] vs. control, respectively, P<0.05).

EXAMPLE 8

Feeding Trials Using Varying Enzymatic Activity

A dry crude enzyme extract produced according to methods described herein is composed primarily of keratinase enzyme, but may also contain other types of compounds, including other enzymes, carbohydrates, non-enzymatic peptides, nucleotide fragments, etc., which have a molecular weight of greater than 5 kDa and are therefore retained upon ultrafiltration.

Additional experiments were conducted to study the correlation between the growth performance of broiler chicks and the keratinase activity of the crude enzyme extracts added to their diets.

Crude enzyme extracts obtained from fermentation production of B. licheniformis strains P1, P2 and T399 were used in these studies and the results are provided in Table 1.

TABLE 1

| Trial # | Crude Enzyme Extract Type | Enzyme Activity (Unit/g) | Inclusion Rate (%) | Growth Performance |
|---|---|---|---|---|
| MT 301 | P1 strain (in 0.5% soy flour)$^1$ | 1,000,000 | 0.05 | No effect |
| | | | 0.10 | Improvement (0.05 < P < 0.1) |
| | | | 0.15 | Improvement (0.05 < P < 0.1) |
| MT 401 | P1 strain (in 0.5% soy flour)$^2$ | 1,000,000 | 0.05 | Significant improvement in low protein |
| | | | 0.10 | Significant improvement in low protein |
| | | | 0.15 | Significant improvement in low protein |
| MT 501$^1$ | P1 strain (in 0.5% soy flour)$^1$ | 1,000,000 | 0.10 | Significant improvement in low protein and control |
| MT 701 | P1 strain (in 0.5% soy flour)$^1$ | 300,000 | 0.25 | Negative effect |
| | P2 strain (in 0.5% soy flour)$^1$ | 450,000 | 0.17 | Slight improvement |

TABLE 1-continued

| Trial # | Crude Enzyme Extract Type | Enzyme Activity (Unit/g) | Inclusion Rate (%) | Growth Performance |
|---|---|---|---|---|
| MT 801 | P1 strain (inhibited by PMSF)[3] | 300,000 | 0.25 | No effect |
| | P1 strain (inactivated by heat)[4] | 300,000 | 0.25 | No effect |
| MT 901 | P2 strain (in 1% soy flour)[1] | 450,000 | 0.10 | Significant improvement |
| | P2 strain (in 2%, 1% soy flour)[1] | 800,000 | 0.10 | No effect |
| | T399 strain (in 2%, 1% soy flour)[1] | <5000 | 0.10 | No effect |
| KE 202 | P2 strain (in 1% soy flour)[1] | 600,000 | 0.10 | Improvement in 23% diets |
| | P2 strain (in 2% soy flour)[1] | 600,000 | 0.10 | Improvement in 21 & 23% diets |
| KE 302 | P1 strain[5] | 150,000 | 0.10 | Significant improvement in all |
| Pilot | P1 strain[1] | 300,000 | 0.10 | Improvement in 21% diet |
| Test | P1 strain[1] | 300,000 | 0.25 | Improvement in 21% diet |

[1]Enzyme supplement fed from 6 to 21 days of age.
[2]Enzyme supplement fed from 6 to 27 days of age.
[3]>90% enzymatic activity is inhibited.
[4]>98% enzymatic activity is inhibited.
[5]Enzyme supplement fed from 1 to 21 days of age.

The foregoing examples are illustrative of the present invention, and are not to be construed as limiting thereof. The invention is described by the following claims, with equivalents of the claims to be included therein.

What is claimed is:

1. An animal feed consisting essentially of:
    (a) a Bacillus licheniformis PWD-1 keratinase;
    (b) one or more protein sources; and
    (c) one or more carbohydrate sources,
wherein the animal feed is essentially free of keratin.

2. An animal feed consisting essentially of:
    (a) a Bacillus licheniformis PWD-1 keratinase;
    (b) one or more protein sources;
    (c) one or more carbohydrate sources; and
    (d) one or more other substances selected from the group consisting of one or more vitamins, one or more minerals, one or more fats, and one or more antibiotics,
wherein the animal feed is essentially free of keratin.

3. The animal feed of claim 1, wherein the one or more protein sources is selected from the group comprising soybean, wheat, rapeseed, or canola.

4. The animal feed of claim 1, wherein the one or more carbohydrate sources is selected from the group comprising corn, oats, barley, sorghum.

5. The animal feed of claim 1, wherein the animal feed is a poultry feed, a pig feed, a cat feed, a dog feed, a ferret feed, an avian feed, or the feed of other monogastric animals.

6. A poultry feed comprising Bacillus licheniformis PWD-1 keratinase, wherein the poultry feed is
    (a) essentially free of keratin, and
    (b) comprises less than about 23% crude protein.

7. The poultry feed of claim 6, wherein the poultry feed is:
    (a) essentially free of keratin, and
    (b) comprises between about 20.23% and about 23% crude protein.

8. The poultry feed of claim 6, wherein the poultry feed is:
    (a) essentially free of keratin, and
    (b) comprises between about 16.80% and about 20.23% crude protein.

9. A poultry feed comprising Bacillus licheniformis PWD-1 keratinase, wherein the poultry feed is:
    (a) essentially free of keratin, and
    (b) comprises less than about 3201 kcal/kg of metabolizable energy.

10. The poultry feed of claim 9, wherein the poultry feed is:
    (a) essentially free of keratin, and
    (b) comprises between about 3050 kcal/kg to about 3201 kcal/kg of metabolizable energy.

11. A method for improving the digestibility of an animal feed essentially free of keratin, the method comprising contacting the feed with Bacillus licheniformis PWD-1 keratinase.

12. A method for improving the feed conversion ratio of an animal feed essentially free of keratin, the method comprising contacting the feed with Bacillus licheniformis PWD-1 keratinase.

13. A method for reducing the anti-nutritional content of an animal feed essentially free of keratin, the method comprising contacting the feed with Bacillus licheniformis PWD-1 keratinase.

14. A method for increasing the metabolizable energy of an animal feed essentially free of keratin, the method comprising contacting the feed with Bacillus licheniformis PWD-1 keratinase.

15. A method for improving the nutritional value of an animal feed essentially free of keratin, the method comprising contacting the feed with Bacillus licheniformis PWD-1 keratinase.

16. The animal feed of claim 1, wherein the animal feed is added to a starter diet, wherein said starter diet is low in protein.

17. The animal feed of claim 1, wherein the animal feed is added to a starter diet, wherein said starter diet is essentially free of keratin.

18. The animal feed of claim 1, wherein the animal feed is a grower diet, wherein said grower diet is low in protein.

19. The animal feed of claim 1, wherein the animal feed is a grower diet, wherein said grower diet is essentially free of keratin.

20. The animal feed of claim 1, wherein the animal feed is a finisher diet, wherein said finisher diet is low in protein.

21. The animal feed of claim 1, wherein the animal feed is a finisher diet, wherein said finisher diet is essentially free of keratin.

* * * * *